(12) United States Patent
Sayama

(10) Patent No.: US 7,160,282 B2
(45) Date of Patent: Jan. 9, 2007

(54) DISPOSABLE WEARING ARTICLE

(75) Inventor: Yasushi Sayama, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 520 days.

(21) Appl. No.: 10/192,289

(22) Filed: Jul. 10, 2002

(65) Prior Publication Data

US 2003/0023225 A1    Jan. 30, 2003

(30) Foreign Application Priority Data

Jul. 24, 2001    (JP)    ............................ 2001-223531

(51) Int. Cl.
*A61F 13/494*    (2006.01)
*A61F 13/49*    (2006.01)

(52) U.S. Cl. .................... 604/385.28; 604/385.27; 604/385.26; 604/385.25; 604/385.24; 604/385.23; 604/385.21; 604/385.3

(58) Field of Classification Search ........... 604/385.04, 604/385.23–385.27, 385.28, 385.21, 385.3
See application file for complete search history.

(56) References Cited

U.S. PATENT DOCUMENTS 5,167,653 A * 12/1992 Igaue et al. ............ 604/385.04
H1630 H * 1/1997 Roe et al. ............. 604/385.28
5,669,896 A * 9/1997 Kielpikowski ......... 604/385.28
5,814,035 A * 9/1998 Gryskiewicz et al. .. 604/385.21
6,010,586 A * 1/2000 Suprise ...................... 156/73.1
6,045,545 A    4/2000 Villez et al.
6,121,510 A * 9/2000 Sauer ......................... 604/378
6,706,029 B1 * 3/2004 Suzuki et al. .......... 604/385.28
2003/0002357 A1 * 1/2003 Kwon et al. ................. 365/194

FOREIGN PATENT DOCUMENTS

| EP | 0 346 477 | 12/1989 |
|---|---|---|
| EP | 1 101 477 | 5/2001 |
| JP | 9-173381 | 7/1997 |

* cited by examiner

*Primary Examiner*—Tatyana Zalukaeva
*Assistant Examiner*—Keshia Gibson
(74) *Attorney, Agent, or Firm*—Butzel Long

(57) ABSTRACT

A disposable wearing article includes a liquid-pervious topsheet, a liquid-impervious backsheet, a liquid-absorbent base panel interposed between these two sheets, a pair of side flaps lying outside transversely opposite side edges of the base panel so as to extend in a longitudinal direction, a pair of leak-barrier cuffs attached to the respective side flaps, elastic members secured to distal side edge portions of the cuffs. The article further includes a pair of liquid-absorbent side panels attached to opposed surfaces of the leak-barrier cuffs.

8 Claims, 4 Drawing Sheets

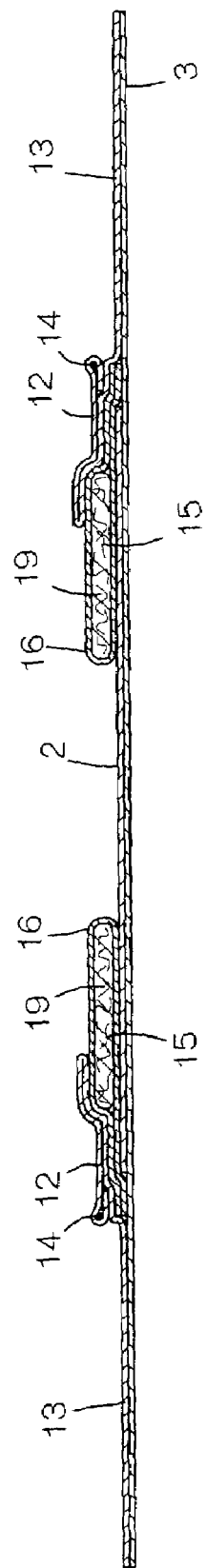

DISPOSABLE WEARING ARTICLE

BACKGROUND OF THE INVENTION

This invention relates to a disposable wearing article for absorption and containment of bodily discharges.

Japanese Patent Publication No. 1997-173381A discloses a disposable diaper of open-type composed of a front waist region, a rear waist region and a crotch region extending between these waist regions. This diaper comprises a liquid-pervious topsheet facing the wearer's body, a liquid-impervious backsheet facing a garment the wearer puts on, a liquid-absorbent base panel interposed between these sheets and extending across the crotch region into the front and rear waist regions, a pair of liquid-absorbent side panels extending outside transversely opposite side edges of the base panel in a longitudinal direction and a pair of leak-barrier cuffs extending outside respective outer side edges of the side panels extending in the longitudinal direction. The side panels are interposed between the top- and backsheets.

With this diaper of prior art, the side panels slightly turn up in the vicinity of the outer side edges thereof as the leak-barrier cuffs rise on the topsheet. This diaper is effective to avoid the anxiety that bodily discharges might leak sideways from the crotch region even when a width of the base panel is dimensioned to be relatively small. This is because the presence of the side panels ensures the crotch region to maintain its desired absorbing capacity and, in addition, the leak-barrier cuffs form barriers against bodily discharges.

In the case of the diaper disclosed in the above-cited Publication, the leak-barrier cuffs are spaced outward from the respective outer side edges of side panels by a given dimension in the transverse direction. With such an arrangement, it can not be expected that the side panels rise in the same manner as the leak-barrier cuffs and form the barriers against bodily discharges even when the leak-barrier cuffs rise on the topsheet. While it is possible for this diaper to avoid the anxiety that bodily discharges might leak sideways from the crotch region, the amount of bodily discharges exceeding the absorbing capacity of the first and side panels and having reached the leak-barrier cuffs may flow along the opposed surfaces of the respective leak-barrier cuffs from the crotch region into the front and rear waist regions, i.e., spread in the longitudinal direction.

SUMMARY OF THE INVENTION

An object of this invention is to provide a disposable wearing article improved so that liquid-pervious panels may rise together with leak-barrier cuffs to form barriers against bodily discharges so that these leak-barrier cuffs may effectively prevent bodily discharges from further flowing in a longitudinal direction of the article after having reached the leak-barrier cuffs.

According to this invention, there is provided a disposable wearing article comprising a chassis defining front and rear waist regions and a crotch region extending between these waist regions and a liquid-absorbent base panel extending across the crotch region into the front and rear waist regions, the chassis having a pair of side flaps extending along transversely opposite side edges of the base panel in a longitudinal direction, a pair of liquid-impervious leak-barrier cuffs extending in the longitudinal direction being attached to the side flaps, each of the leak-barrier cuffs respectively having a proximal side edge portion fixed to the side flap and extending the longitudinal direction, a distal side edge portion extending in the longitudinal direction opposed to the proximal side edge portion, upper and lower portions between the proximal and distal side edge portions and longitudinally opposite fixed end portions collapsed outward in a transverse direction and fixed to the front and rear waist regions in such a collapsed state, and stretchable elastic members extending in the longitudinal direction secured in a stretched state to the distal side edge portions of the leak-barrier cuffs.

This invention further comprises liquid-absorbent side panels covered with liquid-pervious sheets and extending in the longitudinal direction are attached to the opposed surfaces of the leak-barrier cuffs so that the leak-barrier cuffs rise on the chassis as the elastic members contract and the side panels also rise on the chassis as the leak-barrier cuffs rise on the chassis.

According to one preferred embodiment of this invention, each of the side panels has a proximal side edge portion joined to the lower position of the associated leak-barrier cuff so as to extend in the longitudinal direction, a distal side edge portion spaced from the associated leak-barrier cuff so as to extend in the longitudinal direction opposed to the proximal side edge portion and longitudinally opposite end portions lying in the front and rear waist regions and collapsed inward in the transverse direction so that the upper portion of the leak-barrier cuff may rise obliquely outward in the transverse direction while the lower portion of the leak-barrier cuff and the side panel obliquely rise inward in the transverse direction.

According to another preferred embodiment of this invention, the leak-barrier cuff has a vertical length larger than a vertical length of the side panel.

According to still another preferred embodiment of this invention, the chassis comprises a liquid-pervious topsheet facing a wearer's body and a liquid-impervious backsheet facing a garment and wherein the base panel is interposed between the topsheet and the backsheet.

BRIEF DESCRIPTION OF THE DRAWINGS

FIG. 4 is sectional view taken along a line IV—IV in FIG. 2.

DETAILED DESCRIPTION OF THE PREFERRED EMBODIMENTS

Details of the disposable wearing article according to this invention will be more fully understood from the description given hereunder, explaining an open-type diaper as an example, in reference to the accompanying drawings.

Figure 1:
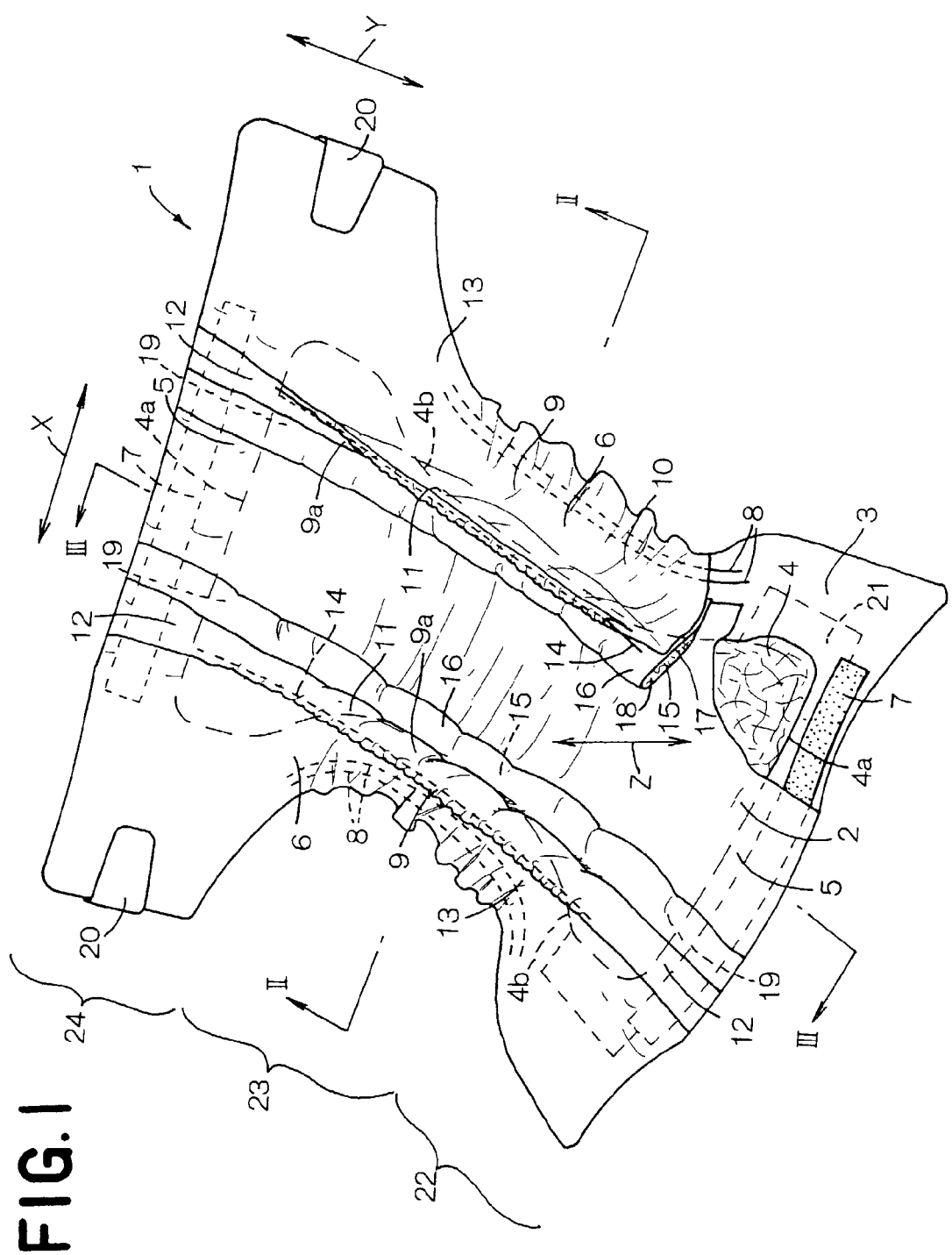
FIG. 1 is a partially cutaway perspective view showing a diaper, viewed from the side of a topsheet.
Figure 2:
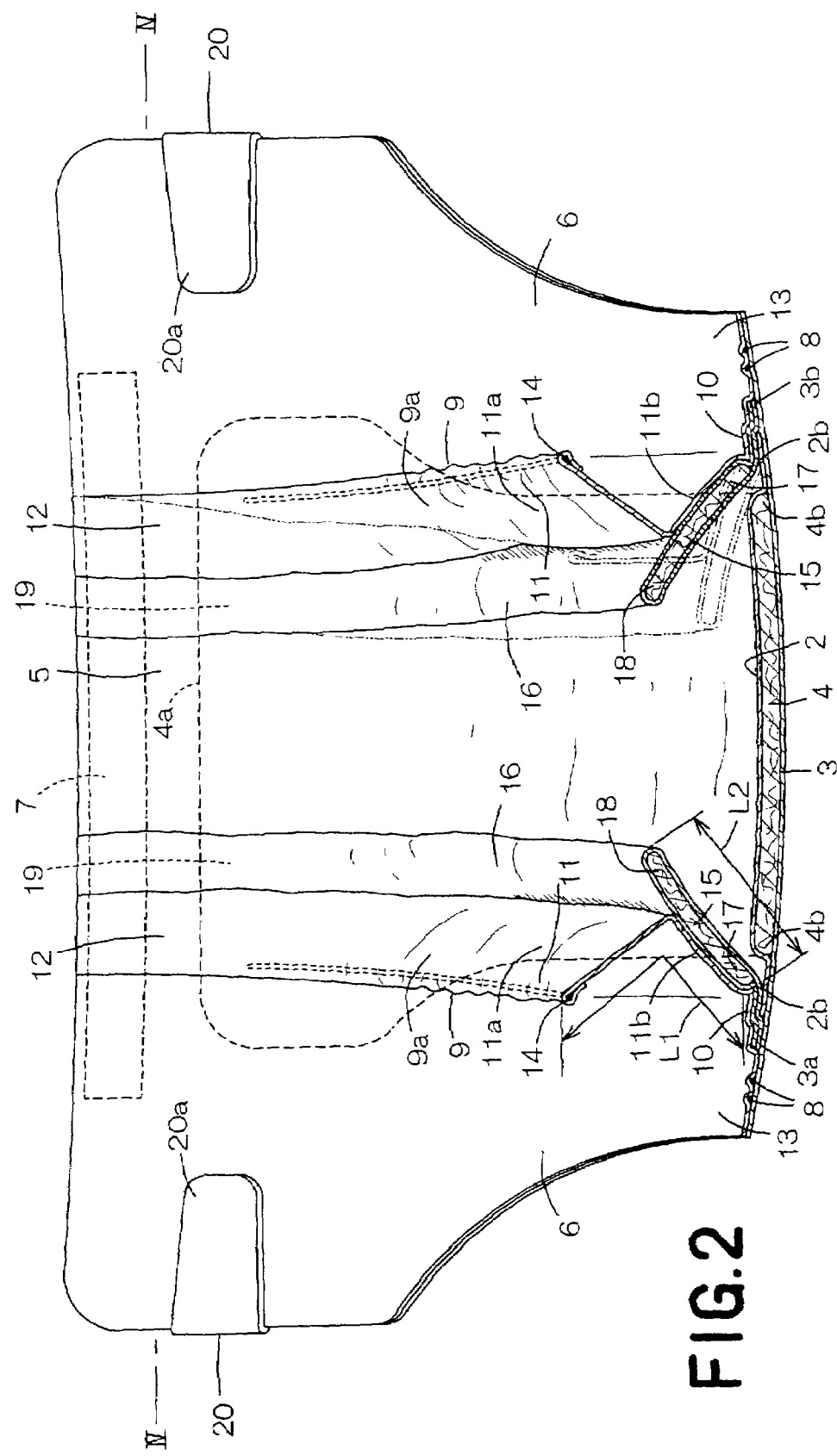
FIG. 2 is a cross-sectional view taken along a line II—II in FIG. 1.
Figure 3:
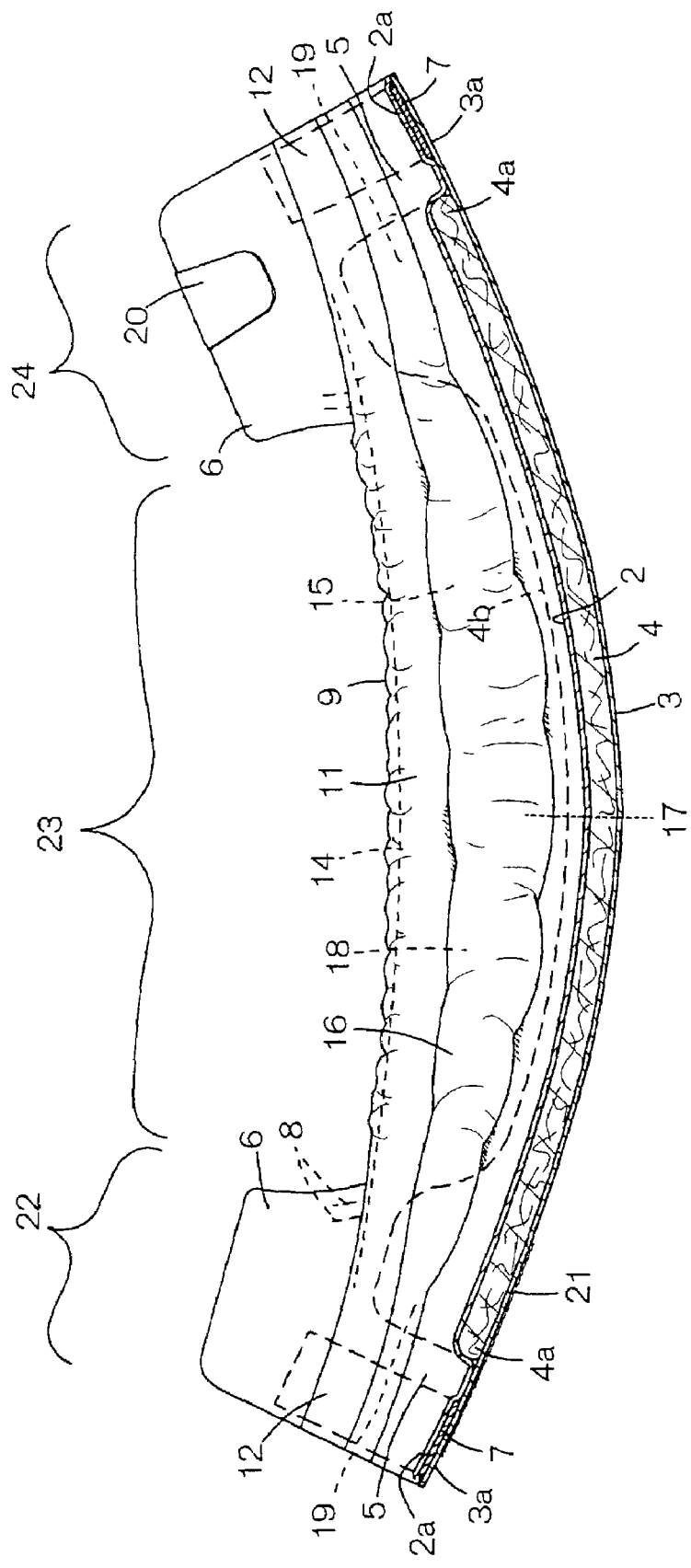
FIG. 3 is a cross-sectional view taken along a line III—III in FIG. 1.

FIG. 1 is a partially cutaway perspective view showing a diaper 1, viewed from the side of a topsheet 2, FIG. 2 is a cross-sectional view taken along a line II—II in FIG. 1, FIG. 3 is a cross-sectional view taken along a line III—III in FIG. 1 and FIG. 4 is a sectional view taken along a line IV—IV in FIG. 2. In FIG. 1, a transverse direction is indicated by an arrow X, a longitudinal direction is indicated by an arrow Y and a vertical direction is indicated by an arrow Z. In FIG. 2, imaginary lines indicated one of side panels 15 collapsed inward in the transverse direction. Expression "inner surfaces" of top- and backsheets 2, 3 should be understood to be the surfaces thereof facing a base panel 4 and expression "outer surface" of these sheets 2, 3 should be understood to be the surfaces thereof facing away from the base panel 4.

The diaper 1 basically comprises a liquid-pervious topsheet 2 facing the wearer's body, a liquid-impervious backsheet 3 facing a garment the wearer puts on and a liquid-absorbent base panel 4 interposed between these sheets 2, 3. The base panel 4 is joined to an inner surface of at least one of the top- and backsheets 2, 3 which form a chassis.

The diaper 1 is composed of, in the longitudinal direction, a front waist region 22, a rear waist region 24 and a crotch region 23 extending between these front and rear waist regions 22, 24. The diaper 1 is provided outside longitudinally opposite ends 4a of the base panel 4 with end flaps 5 extending in the transverse direction and outside transversely opposite side edges 4b of the base panel 4 with side flaps 6 extending in the longitudinal direction. In the crotch region 23 of the diaper 1, the side flaps 6 curve inward in the transverse direction so as to describe circular arcs so that the diaper 1 has an hourglass-shape in its plan view.

The end flaps 5 are respectively provided with waist-surrounding band-like elastic members 7 extending in the transverse direction and secured in a stretched state to these flaps 5. The end flaps 5 are formed with a plurality of gathers as the waist-surrounding elastic members 7 contract inward in the transverse direction. The side flaps 6 are respectively provided with a plurality of thigh-surrounding elastic members 8 extending in the crotch region 23 in the longitudinal direction and secured in a stretched state to these flaps 6. In addition to these elastic members 8, the side flaps 6 are provided with substantially liquid-impervious leak-barrier cuffs 9 extending in the longitudinal direction and attached to these flaps 6.

Each of the leak-barrier cuffs 9 has a proximal side edge portion 10 joined to the associated side flap 6 so as to extend in the longitudinal direction, a distal side edge portion 11 extending in the longitudinal direction opposed to the proximal side edge portion 10, an upper portion 11a and a lower portion 11b between the proximal and distal side edge portions 10, 11 and longitudinally opposite end portions 12 collapsed inward in the transverse direction and joined in such a collapsed state to the front and rear waist regions 22, 24. The leak-barrier cuff 9 additionally has a lateral portion 13 extending outward from the fixed proximal edge portion 10 in the transverse direction. The distal side edge portion 11 has an upper edge thereof provided with a stretchable elastic member 14 extending in the longitudinal direction and secured thereto in a stretched state. The elastic member 14 is covered with a part of the distal side edge portion 11.

Each leak-barrier cuff 9 is provided with each liquid-absorbent side panel 15 which are covered with liquid-pervious sheets 16 and extend in the longitudinal direction of the leak-barrier cuffs 9. Each of the side panels 15 has a proximal side edge portion 17 joined to the lower portion 11b of the leak-barrier cuff 9 so as to extend in the longitudinal direction, a distal side edge portion 18 spaced from the distal side edge portion 11 and extending in the longitudinal direction opposed to the proximal side edge portion 17, and longitudinally opposite fixed end portions 19 lying in the front and rear waist regions 22, 24 and collapsed inward in the transverse direction. These fixed end portions 19 are fixed to the front and rear waist regions 22, 24, respectively, with the liquid-pervious sheet 16 therebetween.

In the diaper 1, the upper portion 11a of the associated leak-barrier cuff 9 and the distal side edge portion 18 of the associated side panel 15 are spaced from each other in the transverse direction. Referring to FIG. 1, the diaper 1 is curved in the longitudinal direction with the topsheet 2 inside, wherein the distal side edge portions 11 of the respective leak-barrier cuffs 9 rise on the topsheet 2 as the elastic members 14 contract inward in the longitudinal direction and the side panels 15 rise on the topsheet 2 as the leak-barrier cuffs 9 rise.

The upper portion 11a of the respective leak-barrier cuffs 9 rise obliquely outward in the transverse direction while the lower portion 11b of the respective leak-barrier cuffs 9 as well as the side panels 15 obliquely rise inward in the transverse direction. The respective leak-barrier cuffs 9 have a vertical dimension L1 larger than a vertical dimension L2 of the side panels 15 and the distal side edge portions 11 extend upward beyond the distal side edge portions 18 of the respective side panels 15 as the upper portion 11a of the respective leak-barrier cuffs 9 are collapsed toward the side panels 15.

The side panels 15 form first barriers against bodily discharges adapted to prevent occurrence of sideway leakage of bodily discharges. The amount of bodily discharges having reached the side panels 15 is reliably absorbed by the side panels 15 through the liquid-pervious sheets 16, so any amount of bodily discharges neither flows nor spreads in the longitudinal direction from the crotch region 23 into the front and rear waist regions 22, 24.

The side panels 15 collapse inward in the transverse direction as indicated by the imaginary lines in FIG. 2, so it is reliably prevented the any amount of bodily discharges might leak sideways from the crotch region 23 even if bodily discharges flow beyond the side panels 15. This is because that the upper portion 11a of the respective leak-barrier cuffs 9 form side barriers.

Even if the upper portion 11a of the leak-barrier cuffs 9 collapse toward the side panels 15, the distal side edge portions 11 extend upward beyond the distal side edge portions 18 of the side panels 15, so it is not likely that any amount of bodily discharges exuding from the side panels 15 might leak beyond the leak-barrier cuffs 9. Even if the base panel 4 has a relatively small dimension in the crotch region 23, the side panels 15 sufficiently compensate the corresponding loss of absorbing capacity of the base panel 4 to ensure the desired absorbing function in crotch region 23.

The transverse dimension of the base panel 4 in the crotch region 23 is preferably in a range of 30–150 mm and the vertical length L1 of the leak-barrier cuffs 9 and the vertical length L2 of the side panels 15 are preferably in a range of 10–50 mm. If the transverse dimension of the base panel 4 is less than 30 mm, the absorbing function of the base panel 4 would be unacceptably deteriorated and it would be difficult to absorb bodily discharges in the crotch region 23. If the transverse dimension of the base panel 4 exceeds 150 mm, the base panel 4 would become bulky in the crotch region of the wearer and the diaper 1 would create a feeling of discomfort against the wearer during use of the diaper 1. If the length L1, L2 of the leak-barrier cuffs 9 and the side panels 15, respectively, are less than 10 mm, the leak-barrier cuffs 9 and the side panels 15 would not adequately function as the barriers against bodily discharges and it would be no more possible to prevent occurrence of sideway leakage of bodily discharges in the crotch region 23.

The longitudinal dimension of the side panels 15 is preferably equal to or slightly smaller than the longitudinal dimension of the base panel 4.

The rear waist region 24 is provided with a pair of tape fasteners 20 extending inward in the transverse dimension. The front waist region 22 is provided on the outer surface of the backsheet 3 with a rectangular target tape strip 21 serving as a landing zone for the tape fasteners 20. Free end portions 20a of the respective tape fasteners 20 are coated with an adhesive (not shown) so that these free end portions 20a may be temporarily fixed to the rear waist region 24 by means of an adhesive.

To wear the diaper 1, the side flaps 6 in the rear waist region 24 are placed upon the outer surfaces of the side flaps 6 in the front waist region 22 and the free end portions 20a of the respective tape fasteners 20 are anchored on the target tape strip 21 to connect the front and rear waist regions 22, 24 with each other. Upon connection between the front and rear waist regions 22, 24, the diaper 1 defines a waist-hole and a pair of leg-holes (both not shown).

In the end flaps 5, longitudinally opposite ends 2a of the topsheet 2 and longitudinally opposite ends 3a of the backsheet 3 are placed upon each other with inner surfaces thereof joined to each other. The waist-surrounding elastic members 7 are interposed between the ends 2a of the topsheet 2 and the ends 3a of the backsheet 3 and bonded to the inner surfaces of these ends 2a, 3a. In the end flaps 5, the fixed end portions 12 of the respective leak-barrier cuffs 9 are bonded to the lateral portions 13 of the leak-barrier cuffs 9 and the liquid-pervious sheets 16 are collapsed inward in the transverse direction and joined to the outer surface of the topsheet 2 in such a collapsed state.

In the side flaps 6, transversely opposite side edge portions 2b of the topsheet 2 extend outward slightly beyond the transversely opposite side edges 4b of the base panel 4 and transversely opposite side edge portions 3b of the backsheet 3 as well as the lateral portions 13 of the respective leak-barrier cuffs 9 extend further outward beyond the side edge portions 2b of the topsheet 2 also in the transverse direction. In the side flaps 6, the liquid-pervious sheets 16 are partially interposed between the side edge portions 2b of the topsheet 2 and the proximal side edge portions 10 of the respective leak-barrier cuffs 9 and joined to them. In the side flaps 6, the side edge portions 3b of the backsheet 3 and the lateral portions 13 of the respective leak-barrier cuffs 9 are placed upon each other and the inner surfaces of these side edge portions 3b and lateral portions 13 are joined together. The thigh-surrounding elastic members 8 are interposed between the side edge portions 3b of the backsheet 3 and the lateral portions 13 of the respective leak-barrier cuffs 9 and bonded to the inner surfaces of these side edge portions 3b and lateral portions 13.

The topsheet 2 and the liquid-pervious sheet 16 may be formed using a material selected from a group including a hydrophilic fibrous nonwoven fabric, a hydrophobic fibrous nonwoven fabric and a plastic film both having a plurality of fine pores. The backsheet 3 and the leak-barrier cuffs 9 may be formed using a material selected from a group including a hydrophobic fibrous nonwoven fabric, a breathable but liquid-impervious plastic film, a composite nonwoven fabric consisting of two or more layers of hydrophobic fibrous nonwoven fabrics laminated one with another and a composite sheet consisting of a hydrophobic nonwoven fabric and a breathable but liquid-impervious plastic film.

It is also possible to form the backsheet 3 and the leak-barrier cuffs 9 using a composite nonwoven fabric comprising a melt blown fibrous nonwoven fabrics having a high water-resistance, sandwiched between spun bond fibrous nonwoven fabrics having high strength and flexibility.

Nonwoven fabric as a stock material for the top- and backsheets 2, 3 may be selected from a group including products obtained by spun lacing, needle punching, melt blowing, thermal bonding, spun bonding, chemical bonding and air-through processes. Component fibers of the nonwoven fabric may be selected from a group including polyolefine, polyester and polyamide-based fibers and core-sheath-type and side-by-side-type conjugated fibers of polyethylene/polypropylene and polyethylene/polyester.

The base and side panels 4, 15 are formed by a mixture of fluff pulp and super-absorbent polymer particles or a mixture of fluff pulp, super-absorbent polymer particles and thermoplastic synthetic resin fibers and compressed to a desired thickness. Preferably, the base panel 4 is entirely covered with and joined to a tissue paper to prevent the base panel 4 from getting out of shape and the polymer particles from falling off from the base panel 4. The polymer particles may be selected from a group consisting of a starch-based polymer, a cellulose-based polymer or a synthetic polymer.

Bonding between the top- and backsheets 2, 3, joining of the base panel 4 to the top- and backsheets 2, 3, securing or the elastic members 7, 8 and joining of the leak-barrier cuffs 9 may be carried out using hot melt adhesives or welding techniques such as a heat-sealing and sonic-sealing.

This invention is applicable, not only to the open-type disposable diaper 1 but also to a pants-type disposable diaper whereto side flaps of front and rear waist regions previously are joined so as to define a waist-hole and a pair of leg-holes.

With the disposable wearing article according to this invention, the liquid-absorbent side panels attached to the respective leak-barrier cuffs rise together with the free side edge portions so as to form the barriers against bodily discharges and thereby to prevent bodily discharges from leaking sideways. In the wearing article according to this invention, the amount of bodily discharges having reached the side panels is absorbed by these side panels and therefore it is not likely that bodily discharges might flow and/or spread in longitudinal direction from the crotch region toward and/or into the front and rear waist regions.

With the embodiment of this invention arranged so that the distal side edge portions of the side panels are spaced from the upper portions of the leak-barrier cuffs, the side panels form the first barriers against bodily discharges so that the side panels may absorb bodily discharges and at the same time prevent sideway leakage of bodily discharges from the crotch region. Even if these side panels collapse inward in the transverse direction and consequently any amount of bodily discharges flows beyond these side panels, the upper portions of the leak-barrier cuffs form the side barriers which reliably prevent sideway leakage of bodily discharges from occurring in the crotch region.

With the embodiment of this invention arranged so that the leak-barrier cuffs have the vertical length larger than the vertical length of the side panels, the leak-barrier cuffs partially extend upward beyond the distal side edge portions of the respective side panels even if the upper portions of the leak-barrier cuffs collapse toward the side panels. In this way, there is no anxiety that the amount of bodily discharges exuding from the side panels might leak out from the leak-barrier cuffs.

What is claimed is:

1. A disposable wearing article comprising:
   a chassis defining front and rear waist regions and a crotch region extending between said waist regions and a liquid-absorbent base panel extending across said crotch region into said front and rear waist regions;
   a pair of side flaps provided on the chassis that extend along transversely opposite side edges of said liquid-absorbent base panel in a longitudinal direction;

a pair of liquid-impervious leak-barrier cuffs extending in said longitudinal direction that are attached to said pair of side flaps, each of said leak-barrier cuffs respectively having:
- a proximal side edge portion fixed to said side flap and extending said longitudinal direction;
- a distal side edge portion extending in said longitudinal opposed to said proximal side edge portion;
- an inner surface that faces toward a transverse center of the chassis;
- upper and lower portions between said proximal and distal side edge portions;
- longitudinally opposite fixed end portions collapsed outward in a transverse direction and fixed to said front and rear waist regions in such a collapsed state; and
- stretchable elastic members extending in said longitudinal direction secured in a stretched state to said distal side edge portions of said leak-barrier cuffs, said disposable wearing article further comprising:
liquid-absorbent side panels covered with liquid-pervious sheets and extending in said longitudinal direction, said liquid-absorbent side panels being attached to opposed inner surfaces of said leak-barrier cuffs so that said leak-barrier cuffs rise on said chassis as said elastic members contract and said liquid-absorbent side panels also rise on said chassis as said leak-barrier cuffs rise on said chassis.

2. The wearing article according to claim 1, wherein each of said liquid-absorbent side panels comprises:
- a proximal side edge portion joined tote lower portion of the associated leak-barrier cuff so as to extend in said longitudinal direction;
- a distal side edge portion spaced from the associated leak-barrier cuff so as to extend in said longitudinal direction opposed to said proximal side edge portion; and
- longitudinally opposite end portions lying in said front and rear waist regions and collapsed inward in said transverse direction while said lower portion of said leak-barrier cuff and said side panel obliquely rise inward in said transverse direction.

3. The wearing article according to claim 1, wherein said leak-barrier cuff has a vertical length that is larger than a vertical length of said side panel.

4. The wearing article according to claim 1, wherein said chassis further comprises:
- a liquid-pervious topsheet facing a wearer's body; and
- a liquid-impervious backsheet facing a garment,
- wherein said base panel is interposed between said topsheet and said backsheet.

5. A disposable wearing article comprising:
a chassis defining front and rear waist regions and a crotch region extending between said waist regions and a liquid-absorbent base panel extending across said crotch region into said front and rear waist regions;
a pair of side flaps provided on the chassis that extend along transversely opposite side edges of said liquid-absorbent base panel in a longitudinal direction;
a pair of liquid-impervious leak-barrier cuffs extending in said longitudinal direction tat are attached to said pair of side flaps, each of said leak-barrier cuffs respectively having:
- a proximal side edge portion fixed to one of said pair of side flaps and extending in said longitudinal direction;
- a distal side edge portion extending in said longitudinal opposed to said proximal side edge portion;
- upper and lower portions between said proximal and distal side edge portions;
- longitudinally opposite fixed end portions collapsed outward in a transverse direction and fixed to said front and rear waist regions in such a collapsed state; and
- stretchable elastic members extending in said longitudinal direction secured in a stretched state to said distal side edge portions of said leak-barrier cuffs, said disposable wearing article further comprising:
liquid-absorbent side panels that comprises liquid-absorbent cores that sit covered by liquid-pervious sheets, said liquid-absorbent side panels extending in said longitudinal direction, said liquid-absorbent side panels being attached to opposed inner surfaces of said leak-barrier cuffs so that said leak-barrier cuffs rise on said chassis as said elastic members contract and said liquid-absorbent side panels also rise on said chassis as said leak-barrier cuffs rise on said chassis.

6. The wearing article according to claim 5, wherein each of said liquid-absorbent side panels comprises:
- a proximal side edge portion joined to the lower portion of the associated leak-barrier cuff so as to extend in said longitudinal direction;
- a distal side edge portion spaced from the associated leak-barrier cuff so as to extend in said longitudinal direction opposed to said proximal side edge portion; and
- longitudinally opposite end portions lying in said front and rear waist regions and collapsed inward in said transverse direction while said lower portion of said leak-barrier cuff and said side panel obliquely rise inward in said transverse direction.

7. The wearing article according to claim 5, wherein said leak-barrier cuff has a vertical length that is larger than a vertical length of said side panel.

8. The wearing article according to claim 5, wherein said chassis further comprises:
- a liquid-pervious topsheet facing a wearer's body; and
- a liquid-impervious backsheet facing a garment,
- wherein said base panel is interposed between said topsheet and said backsheet.

* * * * *